United States Patent [19]
Cecco et al.

[11] Patent Number: 5,453,688
[45] Date of Patent: Sep. 26, 1995

[54] ROTATING PROBE FOR INSPECTING TUBES HAVING AN ECCENTRIC HOUSING FOR SUPPORTING SENSING MEANS

[75] Inventors: Valentino S. Cecco; Werner E. Pantermoller, both of Deep River, Canada

[73] Assignee: Atomic Energy of Canada Limited, Ottawa, Canada

[21] Appl. No.: 110,791

[22] Filed: Aug. 23, 1993

[51] Int. Cl.[6] ............................ G01N 27/82; G01N 27/72
[52] U.S. Cl. .............................................. 324/220; 324/262
[58] Field of Search ................................... 324/219, 220, 324/221, 262

[56] References Cited

U.S. PATENT DOCUMENTS

| | | | |
|---|---|---|---|
| 3,906,358 | 9/1975 | Stone | 324/37 |
| 4,438,399 | 3/1984 | Schnabl et al. | 324/220 |
| 4,581,938 | 4/1986 | Wentzell | 73/623 |
| 4,625,165 | 11/1986 | Rothstein | 324/220 |
| 4,797,613 | 1/1989 | Wentzell | 324/220 |
| 4,937,524 | 6/1990 | Fasnacht et al. | 324/220 |
| 5,134,367 | 7/1992 | Griffith et al. | 324/220 |
| 5,204,622 | 4/1993 | McCaslin et al. | 324/220 |

FOREIGN PATENT DOCUMENTS

| | | | |
|---|---|---|---|
| 926940 | 5/1973 | Canada | 324/48 |
| 942382 | 2/1974 | Canada | 324/48 |
| 1238685 | 6/1988 | Canada | 324/50 |
| 1274277 | 9/1990 | Canada | 324/50 |
| 1277710 | 12/1990 | Canada | 324/50 |
| 0076144 | 4/1983 | European Pat. Off. | |
| 0243082 | 10/1987 | European Pat. Off. | |
| 3282361 | 3/1990 | Japan | |
| 4259852 | 9/1992 | Japan | |

*Primary Examiner*—Walter E. Snow
*Attorney, Agent, or Firm*—Gowling, Strathy & Henderson; Eugene E. Proulx

[57] ABSTRACT

A probe used for inspecting tubes or pipes comprises an elongated flexible shaft, a plurality of axially spaced guides on the shaft, the guides being engageable with the inner surface of a tube for maintaining the shaft substantially concentrically disposed within the tube, and a housing for a sensing element, the housing being secured to the shaft for rotation therewith and disposed between a pair of the guides, the housing having a tube contact area for engagement with the inner surface of the tube. The sum of the radial displacement of the contact area from the axis of the shaft of each of the housing and guides is greater than the inner diameter of the tube so as to cause the shaft to urge the housing and the pair of guides in radially opposed directions.

12 Claims, 3 Drawing Sheets

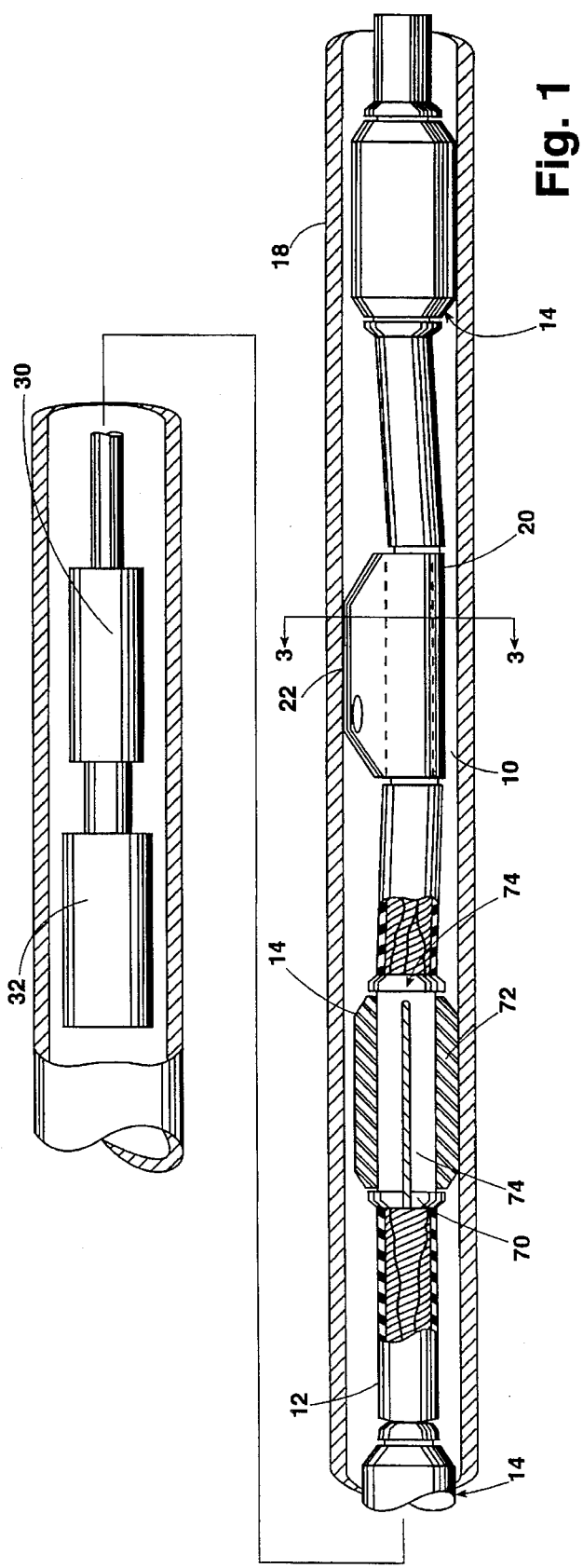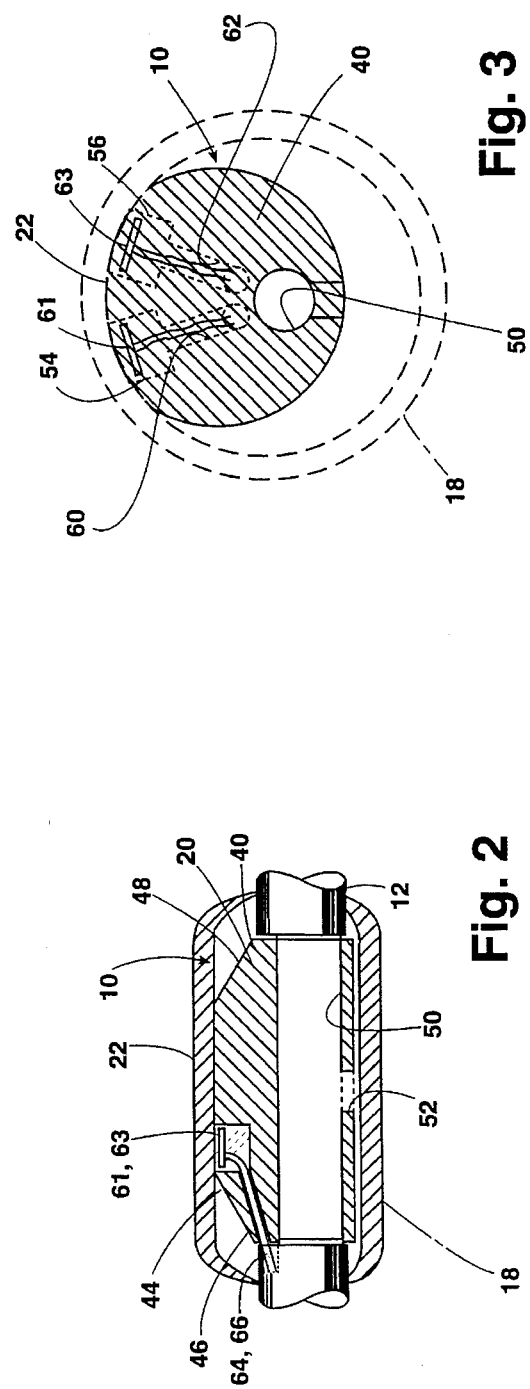

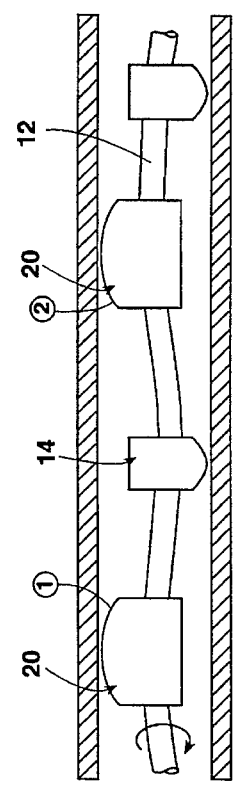
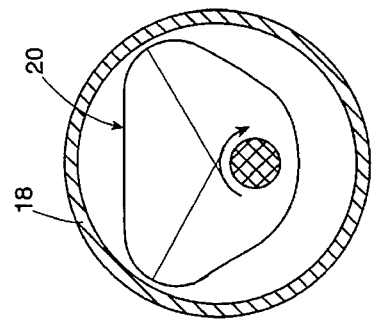
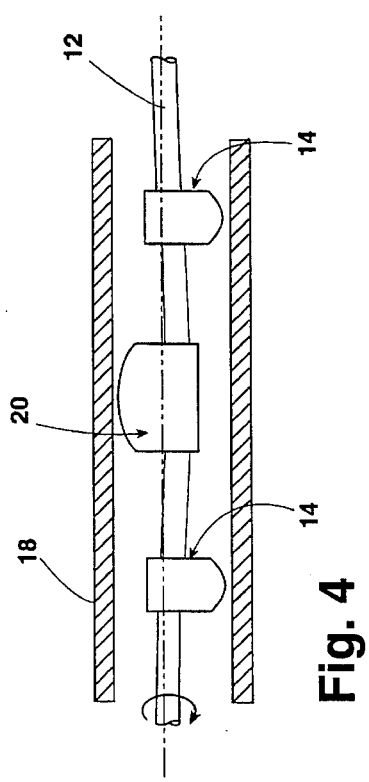
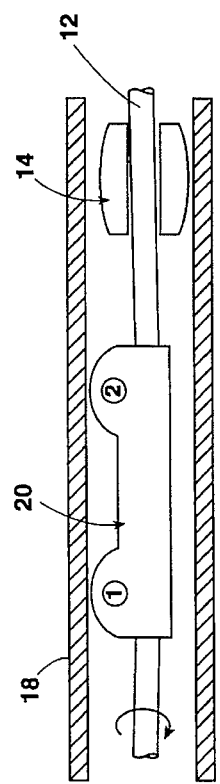

ROTATING PROBE FOR INSPECTING TUBES HAVING AN ECCENTRIC HOUSING FOR SUPPORTING SENSING MEANS

The present invention relates to probes used for inspecting tubes, pipes or the like to sense changes or defects in the tube wall.

BACKGROUND OF THE INVENTION

The use of eddy current probes for inspecting metallic pipes and tubes for flaws and irregularities is well known in the art. By way of background, eddy current probes are devices which carry a transmit or energizing coil, energized by an alternating current signal, for inducing eddy currents in the tube wall proximate the coil and a receive or test coil for detecting the response of the tube wall to eddy currents. The induced eddy currents vary with the structure of the tube. Flaws and irregularities in the tube wall modify the eddy current. The output of the receive coil is monitored to obtain an indication of flaw and/or irregularity location. The probes are inserted into and made to travel along the tube. In some cases, the probe is rotated about an axis paralleling the tube axis so that the entire inner surface of the tube is monitored. In other cases, rather than rotating the probe, a plurality of transmit-receive coil combinations are provided to monitor the entire inner surface area of the tube. The latter devices tend to be more complex, expensive and not as effective. Common disadvantages of existing rotatable eddy current probes are that they have difficulty rotating in deformed or dirty tubes, the probes tend to wear out relatively quickly and they do not have or provide adequate space for the transmit-receive coils.

A known rotatable eddy current probe employs a flexible cable with a plurality of guides mounted on the cable at equal axial intervals therealong. The guides serve to keep the cable substantially concentrically disposed within the tube. One end of the cable is connected to a motor and slip-rings by a quick disconnect mechanism. A probe housing and slip-rings is secured to the cable between two guides. The housing comprises a main body portion which is non-rotatably secured to the cable. The main body portion houses a radially movable portion and a coil spring which urges the movable portion radially outwardly. The movable portion has a tube contact section and carries at least one eddy current probe. When the probe housing is inserted into a tube, the movable portion is urged inwardly by the tube wall against the action of the spring. The spring urges the movable portion and main body portion radially outwardly against diametrically opposed portion of the inner surface of the tube. While this arrangement operates reasonably well, there are a number of disadvantages. The housing requires at least two relatively complex parts—the main body and the movable portion. Thus, the manufacture and assembly of the probe body is relatively expensive. The movable portion, which carries the eddy current coils, is necessarily small and, therefore, offers only a small tube contact area which limits the size and number of coils and considerably increases the wear rate of the probe housing. Since the probe includes moving parts, the probe cannot be made of metallic parts, otherwise false eddy currents would be generated when there is relative movement of the parts. As a consequence, parts tend to wear out more quickly than they would if made of metal. The housing necessarily occupies a substantial portion of the tube. As a result, the operation of the probe will be subject to dirt and obstructions present in the tube. Dirt may become lodged in the housing and prevent proper movement of the movable portion.

There is a need for a probe body which is simpler to make and assemble, has a lower wear rate and, therefore a longer life, occupies less cross sectional area while at the same time providing a relatively large tube contact area so as to increase the sensitivity and life of the device.

SUMMARY OF THE INVENTION

The present seeks to provide a rotatable probe housing which is of simple and inexpensive construction, has no moving parts and, provides improved rotation and wear characteristics and permits the use of laterally or circumferentially displaced transmit and receive coils. While the prior devices have relied upon springs to urge sensors into close proximity with the tube wall, the present invention relies on the natural resilience of the flexible drive cable to provide the resilience required. As a result, it is possible to provide a one-piece probe body. The housing is secured to the cable between two axially displaced guides. It is formed with cavities to receive the sensors. Since the cavities are formed in the main portion of the housing, the tube contact area can be relatively large resulting in longer life and ample room for circumferentially spaced sensing element(s). Further, the housing need not occupy a substantial portion of the cross sectional area of the tube thus enabling the housing easier movement passed obstructions and curves in the tube. Since the probe does not have any moving parts, dirt cannot affect its operation.

The present invention is generally described as a probe used for inspecting tubes or pipes comprises an elongated flexible shaft, a plurality of axially spaced guides on the shaft, the guides being engageable with the inner surface of a tube for supporting the shaft within the tube, and a housing for a sensing element, the housing being secured to the shaft for rotation therewith, disposed between a pair of guides and having a tube contact area for engagement with the inner surface of the tube. The sum of the radial displacement of the contact area from the axis of the shaft of each of the housing and the pair of guides is greater than the inner diameter of the tube so as to cause the shaft to urge the housing and the pair of guides in radially opposed directions.

BRIEF DESCRIPTION OF THE DRAWINGS

These and other features of the invention will become more apparent from the following description in which reference is made to the appended drawings wherein:

FIG. 1 is a longitudinal cross-sectional view of the preferred embodiment of the invention within a tube;

FIG. 2 is a longitudinal cross-sectional view the probe housing of the preferred embodiment of the present invention;

FIG. 3 is a transverse cross-sectional view taken along line 3—3 of FIG. 2;

FIGS. 4, 5 and 6 are schematic longitudinal cross-sectional views, similar to FIG. 1, illustrating alternative embodiments of the present invention;

FIG. 7 is a schematic, transverse cross-sectional view similar to FIG. 2, but illustrating an alternative cross-sectional housing shape.

DESCRIPTION OF PREFERRED EMBODIMENT

Figure 8:
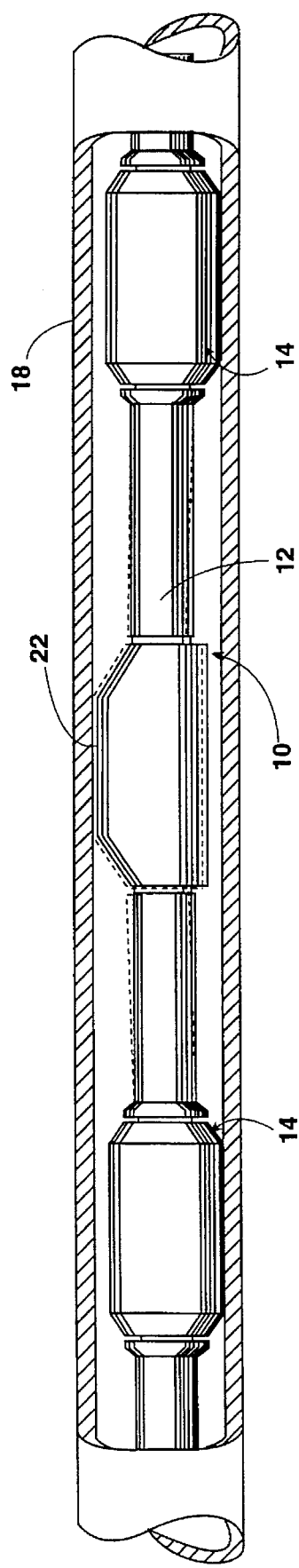

FIGS. 1, 2 and 3 illustrate a rotatable eddy current probe 10 according to the preferred embodiment of the present invention in which the portion of a flexible drive cable which supports a sensing element housing is radially displaced when the probe is inserted into a tube so as to cause the drive cable to resiliently urge the housing against the tube wall. Probe 10 includes an elongated flexible shaft 12, a plurality of axially spaced guides 14 mounted on the shaft and engageable with the inner surface of a tube 16 for supporting the shaft within a tube 18, and a housing 20 for one or more sensing elements. The housing is secured to the shaft for rotation therewith and is disposed between a pair of the guides. The housing is formed with a tube contact area 22 for engagement with the inner surface of the tube. The housing and the aforementioned pair of guides are dimensioned to radially displace or bend the portion of the cable between the pair of guides. As a result, the inherent stiffness in the cable resiliently urges the probe body and guides apart and in engagement with the inner surface of the tube. More specifically, the sum of the radial displacement of the contact area of each of the housing and the pair of guides from the axis of the shaft is greater than the inner diameter of the tube.

Shaft 12 is in the form of a round cross-section, braided cable formed of spring material, as is known in the art. One end of the cable is terminated at a quick disconnect 30 for attachment to a motor 32 in a manner well known in the art.

Housing 20 is a generally cylindrical body 40 with a nominal diameter which is substantially less than but more than one half of the inner diameter of tube 18 to allow the probe body to be displaced radially inwardly by restrictions and or corners in the pipe. The housing is formed with a cylindrical pipe contact area 22, the curvature of which is substantially the same as the curvature of the inner surface of the pipe. As compared with the contact area which would be provided by the surface of remainder of the probe body, this provides a larger contact area which reduces wear and permits a pair of transmit-receive coils to be laterally or circumferentially displaced from one another in the probe body. The opposed ends of the radial outer side 44 of the probe body are tapered at 46 and 48, as shown, to facilitate entry to and egress from the pipe and passage of the probe through restricted areas and corners. The probe body is formed with a throughbore 50 which is parallel to the axis of the probe body, and the pipe axis when the probe is in situ, and on the diametrically opposite side of the body from pipe contact area 22. The cable passes through bore 50 and is secured in position therein in any suitable manner. In the illustrated example, as best shown in FIGS. 2 and 3, a radial hole 52 is drilled through to bore 50 for receiving an epoxy so as to adhesively secured the body to the cable. It has been found that this form of attachment is quite adequate for the torsional, radial and axial loads encountered during operation. The body is also formed with a pair of cavities in the form of drilled holes 54 and 56 which open in the tube contact area for receiving sensing elements and drilled holes 60 and 62 extending from holes 54 and 56, respectively, to one end of the housing, as best shown in FIG. 2. Holes 54 and 56 serve as passageways for feeding electrical conductors to the cavities. The housing may be made of any wear resistant material, including metals. However, when eddy current coils are used, the housing is made of a high resistivity material, such as a titanium alloy, in order to reduce eddy current losses.

It is to be noted that the sensing mechanism forms no parts of the present invention. While an eddy current probe is described herein, this is for illustration purposes only. Thus, it is to be understood that the invention is equally applicable to other forms of testing such as ultrasonic testing where an ultrasonic transducer would replace or supplement the eddy current coils. An energizing or transmit coil 61 and a test or receive coil 63 are placed in the holes 54 and 56, respectively, and are connected to electrical conductors 64 and 66, respectively, which pass through aforementioned holes 60 and 62 and emerge from the probe body adjacent cable 18. Holes 54 and 56 are filled with an epoxy to hold the coils in position in their respective cavities. The conductors are secured to and extend along the cable to the remote end thereof where an electrical current is applied to conductor 64 to energize the transmit coil and the output of the receive coil is detected and analyzed. The transmit and receive coils and the manner in which they are energized and analyzed are well known in the art and, accordingly, their construction and operation are not described in detail herein.

All of the guides 14 are of same construction and formed of any suitable wear resistant material. A suitable number of guides are positioned at approximately equal intervals along the shaft to adequately support the shaft within the tube. In the preferred embodiment, each guide is comprised of a split bushing 70, which is slipped onto the shaft and secured in position by an epoxy, and a cylindrical sleeve 72 which is slipped onto the bushing and held thereon by stops 74 at the opposed ends of the bushing. The sleeve is free to rotate on the bushing. The outer surface of the sleeve engages the inner surface of the tube. Conductors 64 and 66 preferably pass axially through the bore of the bushing. Thin flexible rubber tubes 80 are positioned on the shaft between the guides to protect the electrical conductors.

As already mentioned, the housing and the aforementioned pair of guides are dimensioned to radially displace or bend the portion of the cable between the pair of guides. Specifically, the sum of the radius of sleeve 72 and the radius of cylindrical pipe contact area 22 is arranged to be greater than the inner diameter of tube 18. As a result, the portion of the flexible shaft between the pair of guides between which the housing is positioned will be radially deflected or displaced. The inherent stiffness in the cable resiliently urges the probe body and guides apart, maintaining the tube contact area of the housing in engagement with the inner surface of the tube. The applied radial force should be low to minimize the frictional loss and probe wear. Since the guide and housing diameters can be accurately controlled, it is possible to easily and accurately control the applied force. In prior art devices which use coil or leaf springs, it is difficult if not impossible to obtain this level of control. The minimum guide and housing diameters are established by the minimum constricted tube diameter through which the probe must pass and still function properly in an undamaged tube.

Since the housing need not engage opposite sides of the tube, as is required in prior art devices, it is possible to pass the probe of the present invention by obstructions which would block prior art devices. Further, since the housing of the present invention does not have any moving parts, dirt and grit which may bind prior art probes have no effect on the probe of the present invention. It will be seen that the flexible connection between the probe body and the guide members, provided by the cable, allows the probe to flexibly accommodate, in three dimensions, restrictions and corners within the pipe. It will also be seen that the arcuate contact area 22 of the probe body permits a pair of coils to be circumferentially or laterally positioned in close proximity with one another and that the larger contact area provided thereby has the additional benefit of reducing the wear rate of the contact area.

It will be understood that the principles and spirit of the present invention can be achieved in other ways. For example, the guides may be of piece construction. At least the two guides adjacent the housing may be formed to be eccentric, as shown in FIG. 4, and secured to the shaft to engage the diametrically opposed side of the tube from the tube contact area of the housing or at other suitable angular intervals. This arrangement would be desirable if it was necessary to increase the clearance between the guides and tube wall. As shown in FIG. 5, it is also possible to preset a bend in the portion of the shaft between the pair of guides between which the housing is positioned. FIG. 6 illustrates a double, axially spaced housing having two sets of eddy current probes or other sensing mechanisms. FIG. 7 illustrates a double, circumferentially spaced arrangement in which two sets of sensing mechanisms are circumferentially spaced.

FIG. 8 illustrates an alternative embodiment of the present invention. The components in this embodiment are identical to those of FIG. 1 and therefore the same reference numerals have been used to designate the same components. Unlike the embodiment of FIG. 1 which relies on radial pre-stressing of the drive cable to urge the housing against the tube wall, this embodiment relies on the centrifugal force produced during rotation of the probe to radially displace the cable and permit housing to engage the tube wall. Thus, in this embodiment, the sum of the radial displacement of the contact area of each of the housing and its adjacent pair of guides from the axis of the shaft is less than or equal to the inner diameter of the tube. Thus, when the probe is inserted into a tube, the contact area of the housing does not or just barely engage the inner surface of the tube wall. This may facilitate insertion of the probe into the tube. Probes of the type with which the present invention is concerned are typically rotated at about 300 rpm. When the probe is rotated, the centrifugal force produced by the eccentric construction of the housing will urge the housing radially outwardly toward and against the inner surface of the tube, against the resistance of the drive cable. It will be understood that the drive cable must be selected to permit this action while still having sufficient torsional stiffness to rotate the probe.

It will be understood that various other modifications and modifications can be made without departing from the spirit of the present invention.

The embodiments of the invention in which an exclusive property of privilege is claimed are defined as follows:

1. A probe for use in inspecting tubes or pipes, comprising: an elongated resilient shaft;
   a plurality of axially spaced guides on said shaft, said guides being engageable with the inner surface of a tube for supporting said shaft within said tube; and
   a housing for a sensing means, said housing being secured to said shaft for rotation therewith and disposed between a pair of said guides, said housing having a tube contact area for engagement with the inner surface of a tube, the sum of the radial displacement of said contact area from the axis of said shaft and the radial displacement of the tube contact section of said guides from the axis of said shaft being greater than the inner diameter of said tube so as to cause said shaft to urge said housing and said pair of guides in radially opposed directions.

2. A probe as defined in claim 1, said housing comprising a unitary body, a bore extending through said body for receiving said shaft and means for securing said bore and said shaft against relative rotation.

3. A probe as defined in claim 2, said body being cylindrical, said bore having an axis paralleling the axis of said body but being radially displaced therefrom.

4. A probe as defined in claim 2, said means for securing being an epoxy resin.

5. A probe as defined in claim 1, said contact area being arcuate in cross section and the radius thereof being substantially the same as the inner radius of said tube.

6. A probe as defined in claim 5, said arcuate contact area extending longitudinally of said body.

7. An eddy current probe as defined in claim 3, said body having tapered axially opposed ends to facilitate passage of said probe body through restrictions and corners.

8. An eddy current probe as defined in claim 1, each said guide means being cylindrical and concentrically disposed on said shaft.

9. A probe as defined in claim 8, each guide means including a bushing secured to said shaft against rotation thereon and a sleeve mounted on said bushing for rotation thereon, said sleeve having an outer cylindrical surface engageable with the inner surface of said tube.

10. A probe as defined in claim 9, said bushing having stops at opposed ends thereof for preventing axial displacement of said sleeve with respect to said bushing.

11. An eddy current probe for use in inspecting tubes or pipes, comprising:
   an elongated resilient shaft having a quick disconnect connector at one end thereof for removably connecting said end to a drive motor;
   a plurality of axially spaced guides on said shaft for supporting said shaft within said tube, each said guide comprising a bushing secured to said shaft against rotation thereon and a sleeve mounted on said bushing for rotation thereon, said sleeve having an outer cylindrical surface engageable with the inner surface of said tube;
   a housing for sensing means, said housing comprising a cylindrical body having a longitudinal bore for receiving said shaft, the axis of said bore being eccentric with respect to the axis of said body, means for securing said housing to said shaft against relative rotation, a tube contact area on the diametrically opposite side of said body from said bore, said tube contact area being arcuate with a radius of curvature which is substantially the same as inner radius of said pipe, a first cavity in said body for receiving an eddy current transmit coil and a second cavity in said body for receiving an eddy current receive coil, said cavities opening in said tube contact area, and a passageway extending from each said cavity to one end of said body for receiving electrical conductors;
   the sum of the radial displacement of said tube contact area from the axis of said shaft and the radius of the sleeves of the guides adjacent said body being greater than the inner diameter of said tube so as to impose a eccentricity in the axis of said shaft with respect to the axis of said tube and thereby cause said shaft to impart diametrically opposed forces to said body and said adjacent guides.

12. A probe for use in inspecting tubes or pipes, comprising:
   an elongated resilient shaft;
   a plurality of axially spaced guides on said shaft, said guides being engageable with the inner surface of a tube for supporting said shaft within said tube; and
   an housing for a sensing means, said housing being secured to said shaft for rotation therewith and disposed between a pair of said guides, said housing being eccentric with respect to the axis of said shaft and having a tube contact area for engagement with the inner surface of a tube, the sum of the radial displacement of said contact area from the axis of said shaft and the radial displacement of the tube contact section of said guides from the axis of said shaft being less than or equal to the inner diameter of said tube;

said shaft having sufficient torsional stiffness to rotate said probe in said tube and a radial stiffness which permits the portion of said shaft between said pair of guides to deflect radially outwardly under the influence of the centrifugal force produced at the normal rotational speed of said shaft so as to permit said housing engage the inner surface of said tube.

* * * * *